(12) United States Patent
Lombardo et al.

(10) Patent No.: US 7,837,710 B2
(45) Date of Patent: Nov. 23, 2010

(54) KNOTLESS SUTURE ANCHOR

(75) Inventors: Giuseppe Lombardo, New Port Richey, FL (US); Drew Amery, Clearwater, FL (US); Peter C Miller, Largo, FL (US)

(73) Assignee: Linvatec Corporation, Largo, FL (US)

( * ) Notice: Subject to any disclaimer, the term of this patent is extended or adjusted under 35 U.S.C. 154(b) by 1090 days.

(21) Appl. No.: 10/937,592

(22) Filed: Sep. 9, 2004

(65) Prior Publication Data
US 2005/0055052 A1    Mar. 10, 2005

Related U.S. Application Data

(60) Provisional application No. 60/502,170, filed on Sep. 10, 2003.

(51) Int. Cl.
*A61B 17/04* (2006.01)
(52) U.S. Cl. .................................. 606/232; 606/300
(58) Field of Classification Search ................. 606/232, 606/300–331; 623/13.14
See application file for complete search history.

(56) References Cited

U.S. PATENT DOCUMENTS

| | | | |
|---|---|---|---|
| 4,750,492 A | 6/1988 | Jacobs | |
| 5,464,427 A | 11/1995 | Curtis et al. | |
| 5,480,403 A * | 1/1996 | Lee et al. | 606/72 |
| 5,545,180 A * | 8/1996 | Le et al. | 606/232 |
| 5,584,835 A | 12/1996 | Greenfield | |
| 5,702,397 A | 12/1997 | Goble et al. | |
| 5,902,321 A | 5/1999 | Caspari et al. | |
| RE36,289 E | 8/1999 | Le et al. | 606/232 |
| 6,086,608 A | 7/2000 | Ek et al. | |
| 6,200,329 B1 | 3/2001 | Fung et al. | 606/232 |

(Continued)

FOREIGN PATENT DOCUMENTS

WO    WO 97/30649    8/1997

(Continued)

*Primary Examiner*—Gary Jackson
*Assistant Examiner*—Gregory Anderson
(74) *Attorney, Agent, or Firm*—Ostrolenk Faber LLP

(57) ABSTRACT

A knotless suture anchor and method for its insertion into tissue are provided. The suture anchor includes an inner member including a proximal shaft and a distal securing member shaped to secure the inner member to the tissue, the proximal shaft including a first locking part and at least one hole extending therethrough for receiving the suture thread; and a collar member including an axial bore shaped to receive the proximal shaft of the inner member, a second locking part, and at least one hole extending therethrough and assigned to the hole of the proximal shaft of the inner member, the collar member being axially slidable into unlocked and locked positions relative to the proximal shaft of the inner member, the collar member being relatively axially slidable into the locked position only to secure the suture thread. The hole of the collar member is aligned with the hole of the proximal shaft of the inner member when the collar member is placed into the unlocked position, the hole of the collar member is misaligned with the hole of the proximal shaft of the inner member when the collar member is placed into the locked position, and the first locking part of the proximal shaft engages with the second locking part of the collar member to axially lock the collar member with respect to the proximal shaft when the collar member is placed into the locked position.

14 Claims, 9 Drawing Sheets

Locked Position

U.S. PATENT DOCUMENTS

| | | |
|---|---|---|
| 6,527,794 B1 | 3/2003 | McDevitt et al. |
| 6,585,730 B1 | 7/2003 | Foerster |
| 6,660,023 B2 | 12/2003 | McDevitt et al. |
| 6,692,516 B2 | 2/2004 | West, Jr. et al. ............. 606/232 |
| 2002/0115999 A1 | 8/2002 | McDevitt et al. |
| 2002/0147463 A1* | 10/2002 | Martinek .................... 606/232 |
| 2004/0133239 A1 | 7/2004 | Singhatat .................... 606/232 |
| 2004/0138706 A1 | 7/2004 | Abrams et al. ............. 606/232 |

FOREIGN PATENT DOCUMENTS

| | | |
|---|---|---|
| WO | WO 01/10312 | 2/2001 |
| WO | WO 02/51325 | 4/2002 |

* cited by examiner

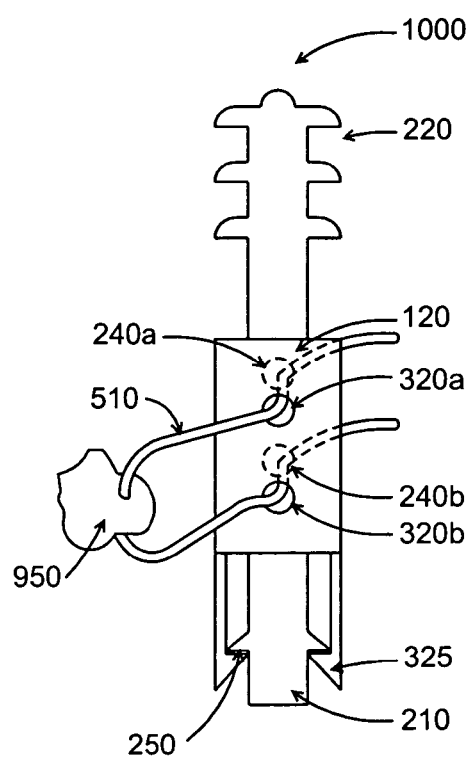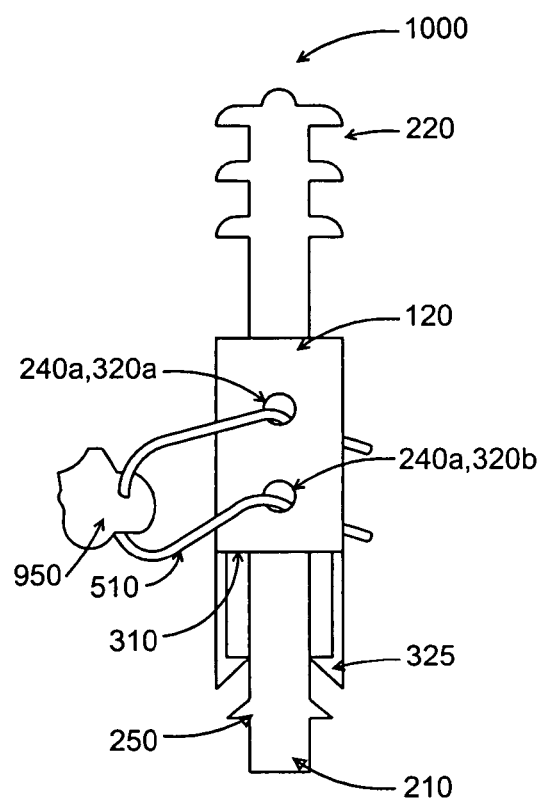
Fig. 8b
Fig. 8a

US 7,837,710 B2

KNOTLESS SUTURE ANCHOR

RELATED APPLICATIONS

The present application is based on and claims priority to U.S. Provisional Application No. 60/502,170 filed on Sep. 10, 2003 and entitled "KNOTLESS BIO-ABSORBABLE SUTURE ANCHOR," the entire contents of which are expressly incorporated herein by reference.

FIELD OF THE INVENTION

The present invention relates to suture or surgical anchors and methods for installing same in tissue. In particular, the present invention relates to a suture anchor for anchoring a second tissue such as soft tissue to a first tissue such as bone without requiring the tying of a knot in the suture.

BACKGROUND INFORMATION

It is common in the medical arts for medical personnel, such as surgeons, to use suture anchors to facilitate the attachment of soft tissue to bone while performing medical procedures. Conventionally, the bone is pre-prepared by drilling a bore hole, within which the suture anchor is subsequently inserted. A suture extending from the anchor is either attached to or threaded through the soft tissue so that the soft tissue may be secured to the bone. Once the soft tissue is secured, the surgeon must tie off or knot the suture to ensure that the soft tissue remains in place after the medical procedure. Alternatively, the suture may be attached to the tissue prior to insertion of the anchor into the bone bore hole. In this case also, a knot must be made in the suture to tie the tissue to the anchor. Often, due to tight clearances, particularly in arthroscopic surgery, it is difficult to manipulate the sutures to tie the knot.

SUMMARY OF THE INVENTION

The present invention relates to a method and device using a suture anchor to attach soft tissue to bone or other tissue which allows the soft tissue to be secured without tying a knot. For this purpose, a knotless suture anchor is provided for anchoring a suture thread to tissue (e.g., bone tissue). The suture anchor includes an inner member including a proximal shaft and a distal securing member shaped to secure the inner member to the tissue, the proximal shaft including a first locking part and at least one hole extending therethrough for receiving the suture thread; and a collar member including an axial bore shaped to receive the proximal shaft of the inner member, a second locking part, and at least one hole extending therethrough and assigned to the hole of the proximal shaft of the inner member, the collar member being axially slidable into unlocked and locked positions relative to the proximal shaft of the inner member, the collar member being axially relatively slidable into the locked position only to secure the suture thread. The hole of the collar member is aligned with the hole of the proximal shaft of the inner member when the collar member is placed into the unlocked position, the hole of the collar member is misaligned with the hole of the proximal shaft of the inner member when the collar member is placed into the locked position, and the first locking part of the proximal shaft engages with the second locking part of the collar member to axially lock the collar member with respect to the proximal shaft when the collar member is placed into the locked position.

The suture is first threaded into the first tissue, forming a suture loop through the first tissue. The two legs of the suture are then inserted through the holes of the collar member and the inner member, and the anchor is inserted into the second tissue. Then, the collar member is moved distally, for example, using a suture anchor insertion tool. This causes the hole of the collar member to come out of alignment with the hole of the inner member, thereby causing the suture to be frictionally secured between the outer surface of the inner member and the inner surface of the collar member. In this manner, the suture may be fixedly secured to the anchor without need for tying a knot in the suture.

BRIEF DESCRIPTION OF THE DRAWINGS

FIGS. 8a to 8d illustrate another exemplary suture anchor according to the present invention, FIGS. 8a and 8c in unlocked positions, and FIGS. 8b and 8d in locked positions.

DETAILED DESCRIPTION

Figure 1:
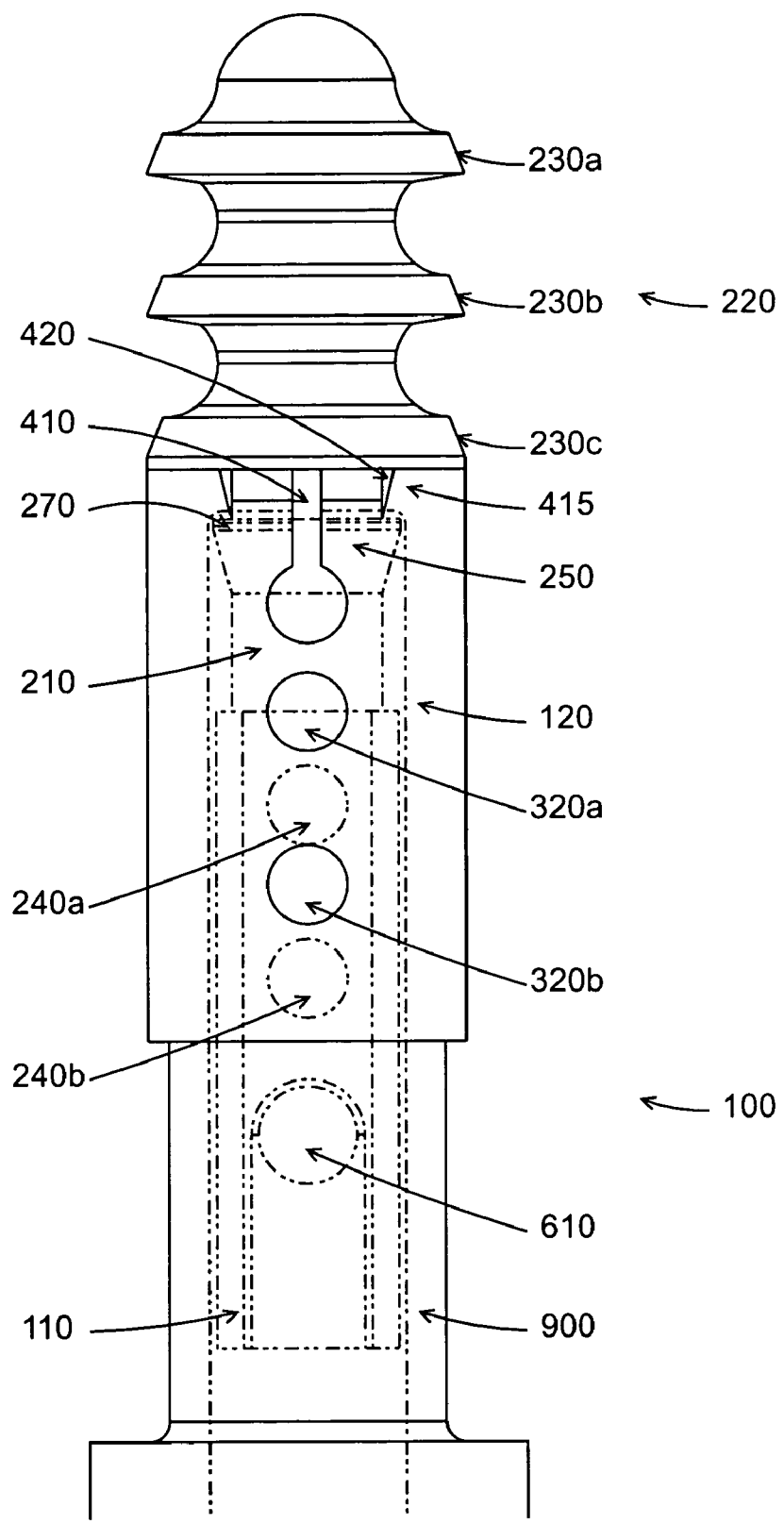
FIG. 1 illustrates a first exemplary knotless suture anchor according to the present invention.

Referring now to FIG. 1, there is seen a first example knotless suture anchor 100 according to the present invention. Suture anchor 100 includes an inner member 110 and a slidable collar member 120 configured to be concentrically disposed about inner member 110. Preferably, knotless suture anchor 100 is made from a bio-absorbable material. However, it should be appreciated that knotless suture anchor 100 may be constructed from any material suitable for securing suture anchor 100 to tissue. For example, suture anchor 100 may be constructed from a non-bioabsorbable and/or bio-compatible material. Insertion tool 900 is provided for inserting knotless suture anchor 100 into tissue and/or for securing a suture to suture anchor 100, in a manner more fully described below.

Figure 2:
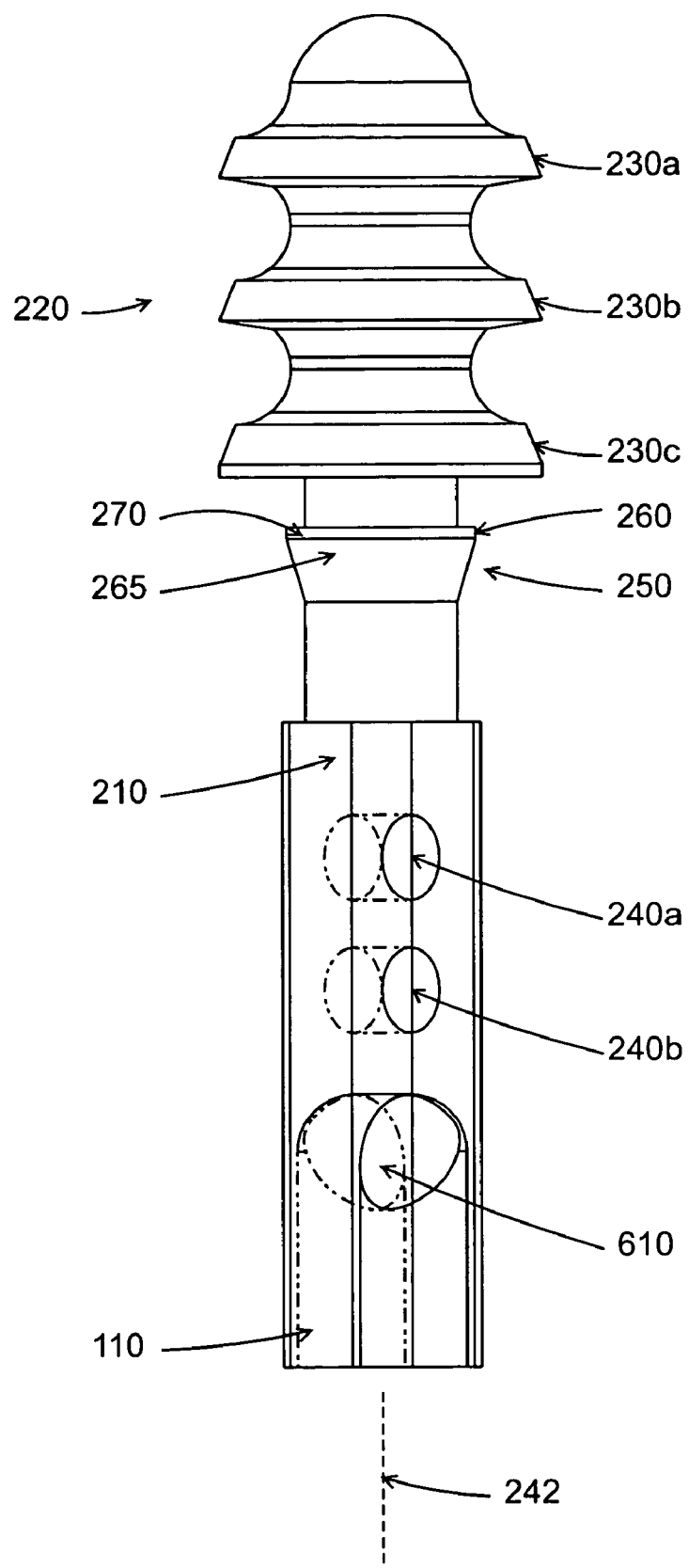
FIG. 2 illustrates an inner member of the knotless suture anchor illustrated in FIG. 1, shown rotated about its axis from the position illustrated in FIG. 1.

Referring also to FIG. 2, inner member 110 includes a proximal shaft 210 for coupling to collar member 120 and a distal securing member 220 for securing suture anchor 100 into tissue 520, for example, bone tissue (see FIGS. 5a to 5f). Distal securing member 220 may include any structure operable to secure knotless suture anchor 100 within tissue. For example, as shown in FIG. 2, distal securing member 220 may include at least one annular rib 230 configured to engage the tissue, thereby preventing knotless suture anchor 100 from being removed after insertion. Although FIG. 2 illustrates distal securing member 220 with three annular ribs 230a, 230b, 230c, it should be appreciated that distal securing member 220 may include any number of annular ribs 230 for securing suture anchor 100 to tissue. It should also be appreciated that distal securing member 220 may include other structures in addition to or in lieu of annular rib 230 for engaging tissue. For example, distal securing member 220 may include at least one barb (not shown) for securing knotless suture anchor 100 into tissue. Distal securing member 220 may also include, for example, at least one suitably dimensioned flange portion (not shown), at least one raised portion (not shown), at least one hooked portion (not shown), or any other structure operable to secure suture anchor 100 to tissue.

Figure 4:
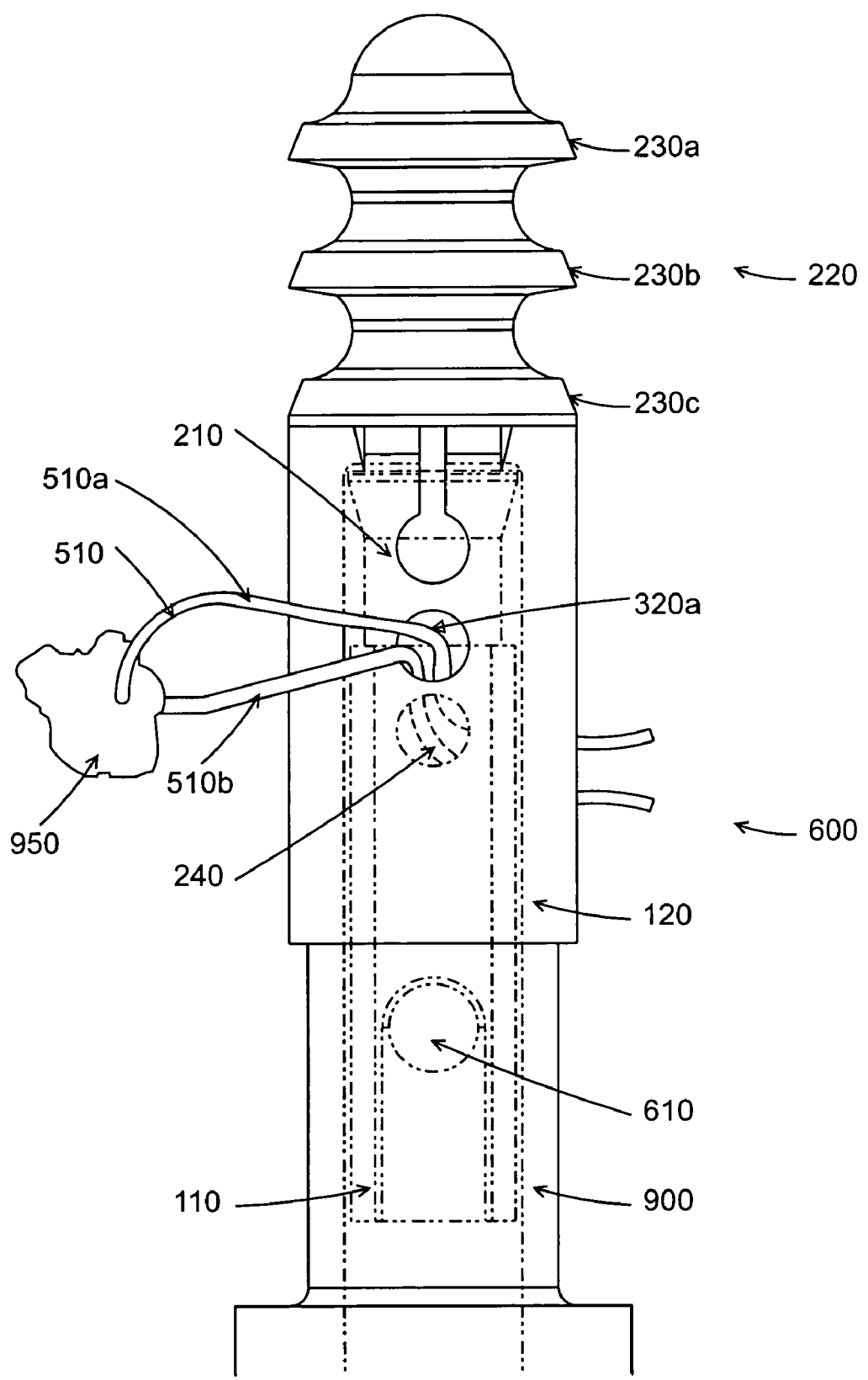
FIG. 4 illustrates another exemplary knotless suture anchor according to the present invention.

Proximal shaft 210 includes two suture holes 240a, 240b extending completely therethrough for receiving respective ends of a suture thread 510 (see FIGS. 5a to 5e). Although FIG. 2 illustrates suture holes 240a, 240b extending through proximal shaft 210 at a right angle to axis 242 of proximal shaft 210, it should be appreciated that suture holes 240a, 240b may extend through proximal shaft 210 at any suitable angle with respect to the axis of proximal shaft 210. It should also be appreciated that proximal shaft 210 may include any number of suture holes 240 for receiving any number of suture threads 510. For example, proximal shaft 210 may include a single suture hole 240 for receiving both ends of suture thread 510, as shown in the embodiment of FIG. 4.

Proximal shaft 210 also includes a first locking part 250 for locking collar member 120 in a manner more fully described below. In the embodiment illustrated in FIG. 2, first locking part 250 includes a flange portion 260 having a sloped proximal surface 265 and a distal locking lip 270. Although inner member 110 illustrated in FIG. 2 includes flange portion 260 for locking proximal shaft 210 to collar member 120, the present invention is not intended to be limited to specific structures of first locking part 250. In this regard, it should be appreciated that first locking part 250 need not include flange portion 260, but rather may include any structure, mechanism, or arrangement, in addition to or in lieu of flange portion 260 that is operable to lock collar member 120 to proximal shaft 210.

Proximal shaft 210 also includes additional hole 610 configured to receive a length of actuating line 620, such as flexible, ultra-high molecular weight polyethylene suture thread (e.g., Dyneema Suture). Actuating line 620 may also include Kevlar, nylon, Spectra and/or any combination of these materials. Actuating line 620 may also comprise, for example, an additional length of suture thread, which may or may not be left inside the body of the patient after insertion of the knotless suture anchor 100. Hole 610 may have a slightly larger diameter than that of suture holes 240a, 240b to accommodate a thicker actuating line 620. However, it should be appreciated that hole 610 may have any diameter relative to that of suture holes 240a, 240b, such as a diameter equal to or smaller than the diameter of suture holes 240a, 240b. The actuating line 620 is used to apply a proximal force on shaft 210 thereby relatively sliding collar member 120 distally with respect to proximal shaft 210 into a locked position, as more fully described below. It should also be appreciated, however, that proximal shaft 210 need not include hole 610 and actuating line 620 for this purpose. Instead, proximal force may be exerted on shaft 210 in other manners, for example, by applying a proximally directed pulling force on a suitably dimensioned tool (not shown) coupled, or engaged with, releasably or otherwise, to proximal shaft 210.

Figure 3:
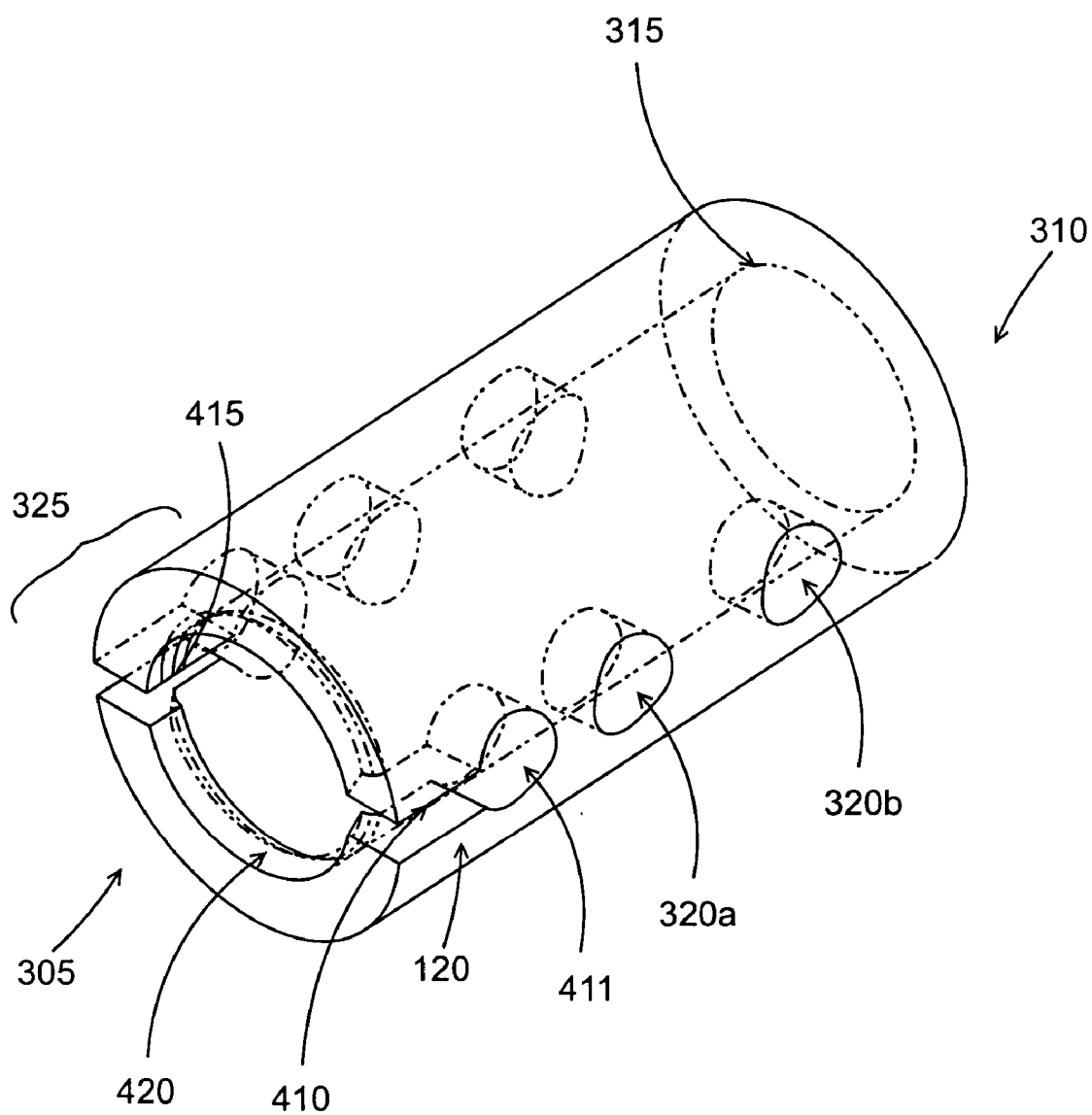
FIG. 3 illustrates a collar member of the knotless suture anchor illustrated in FIG. 1.

Referring to FIG. 3, collar member 120 includes distal and proximal ends 305, 310, an axial bore 315, two suture holes 320a, 320b respectively assigned to suture holes 240a, 240b of proximal shaft 210, and a second locking part 325. Axial bore 315 of collar member 120 is shaped to receive proximal shaft 210 of inner member 110. In this manner, collar member 120 is slidably positionable into at least two positions relative to proximal shaft 210 of inner member 110: (a) an unlocked positioned, in which suture holes 320a, 320b of collar member 120 are aligned with suture holes 240a, 240b of inner member 110; and (b) a locked position, in which suture holes 320a, 320b of collar member 120 are not aligned with suture holes 240a, 240b of inner member 110. Second locking part 325 is configured to couple with first locking part 250 of proximal shaft 210 to axially lock collar member 120 with respect to inner member 110 when collar member 120 is placed into the locked position. Second locking part 325 of collar member 120 includes a slot 410, an annular flange 415 extending radially inward, and a countersink portion 420 (see FIG. 1) formed in the distal end of annular flange 415. As shown in FIG. 3, slot 410 extends proximally into a hole 411. It should be appreciated, however, that slot 410 need not include hole 411. Slot 410 and hole 411 are provided to permit flange 415 to snap over flange portion 260 of proximal shaft 210 to lock collar member 120 into the locked position. Furthermore, although second locking part 325 of FIG. 3 includes slot 410 and annular flange 415 for locking collar member 120 to proximal shaft 210, the present invention described herein is not intended to be limited to specific structures of second locking part 325. In this regard, it should be appreciated that second locking part 325 need not include slot 410 and annular flange 415, but rather may include any structure, mechanism, or arrangement, in addition to or in lieu of slot 410 and annular flange 415, operable to lock collar member 120 to proximal shaft 210.

Figure 5A:
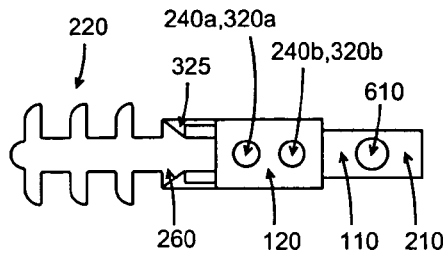
FIGS. 5a to 5e show an operational sequence for inserting a knotless suture anchor into tissue.
Figure 5B:
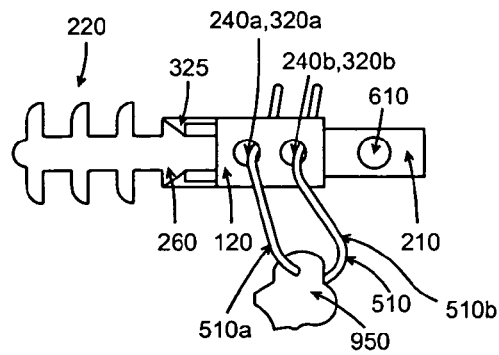
Figure 5C:
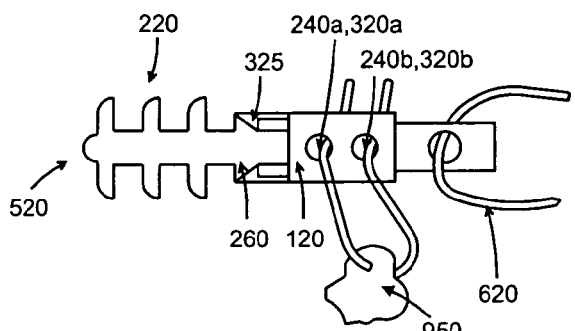
Figure 5D:
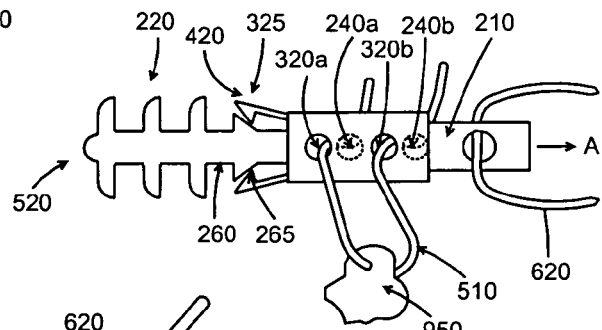
Figure 5E:
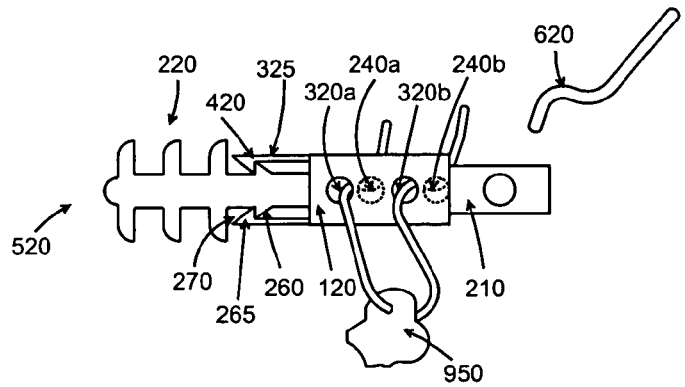
Figure 6A:
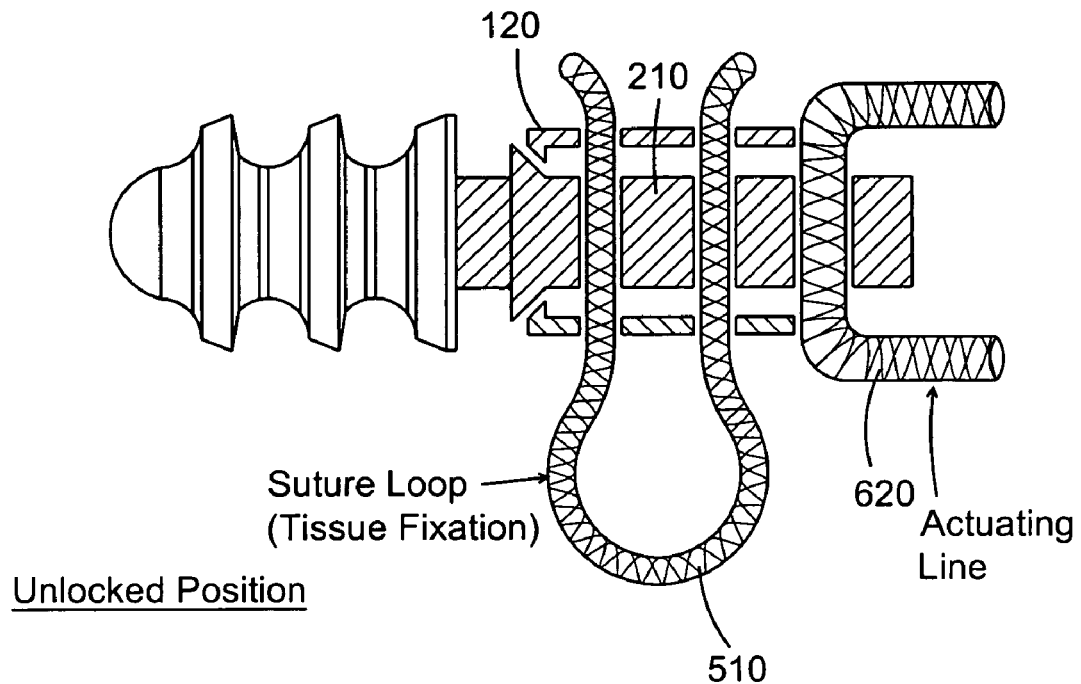
FIGS. 6a and 6b illustratively show how the knotless suture anchor secures the suture.
Figure 6B:
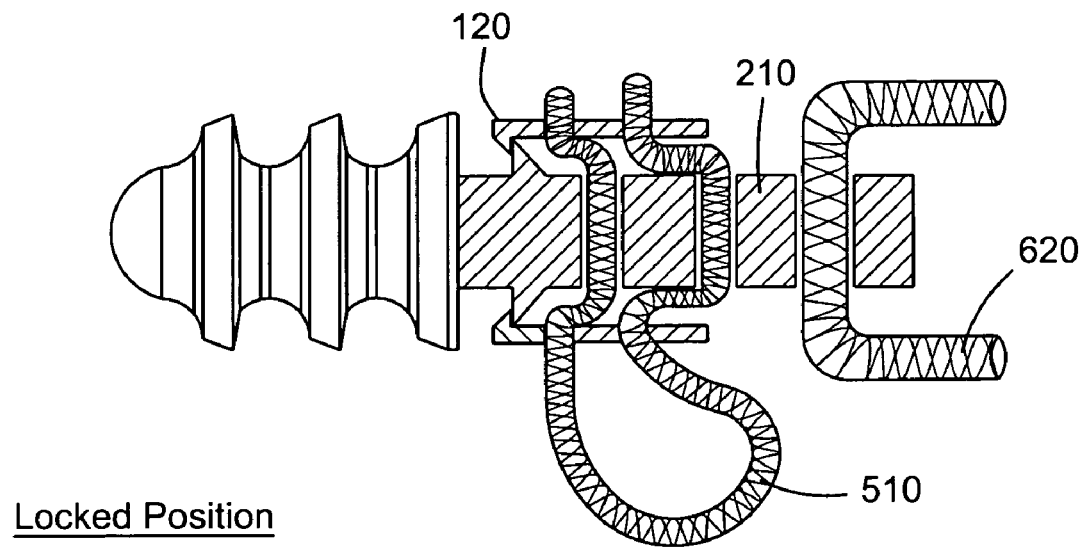

Referring now to FIGS. 5a to 5e, there is seen an operational sequence for inserting knotless suture anchor 100 into tissue (e.g., bone tissue). First, as shown in FIG. 5a, collar member 120 is moved with respect to proximal shaft 210 of inner member 110 into the unlocked position, such that suture holes 320a, 320b of collar member 120 are aligned with suture holes 240a, 240b of inner member 110. Then, as shown in FIG. 5b, a suture leg 510a of a suture thread 510 previously threaded through tissue 950 is inserted through suture holes 240a, 320a of inner member 110 and collar member 120. The other leg 510b of suture thread 510 is inserted through suture holes 240b, 320b of inner member 110 and collar member 120. Next, as shown in FIG. 5c, actuating line 620 is inserted through additional hole 610 and suture anchor 100 is inserted into tissue 520 (e.g., bone tissue). Alternatively, actuating line 620 may be previously inserted or disposed (e.g., at time of sale) through hole 610. Actuating line 620 is preferably made from a high strength thread, such as flexible, ultra-high molecular weight polyethylene suture thread. Once suture anchor 100 is inserted within tissue 520, distal securing member 220 engages tissue 520 to secure suture anchor 100 in place within tissue 520. Then, collar member 120 is relatively moved distally toward first locking part 250 of proximal shaft 210, as shown in FIG. 5d. Collar member 120 may be relatively moved distally, for example, using a suture anchor insertion tool (not shown) configured to engage with collar member 120 for sliding collar member 120 distally with respect to proximal shaft 210. While collar member 120 is slid distally, a proximal force is exerted on both ends of actuating line 620 along direction (A) to ensure that suture anchor 100 remains stationary within tissue 520 while collar member 120 is moved distally into the locked position with respect to proximal shaft 210 of inner member 110. The proximal force exerted on actuating line 620 may be effected by a suitably dimensioned tool (not shown) and/or a surgeon, who may grab both ends of actuating line 620 while distally moving collar member 120 into the locked position. The distal movement of collar member 120 causes suture holes 320a, 320b of collar member 120 to come out of alignment with suture holes 240a, 240b of inner member 110, thereby causing suture 510 to be frictionally secured between the outer surface of proximal shaft 210 and the inner surface of collar member 120, as shown in FIGS. 6a and 6b. As collar member 120 is further displaced distally, countersink portion 420 of annular flange 415 engages sloped proximal surface 265 of flange portion 260 of proximal shaft 210, thereby causing annular flange 415 to extend radially outward from proximal shaft 210, as shown in FIG. 5d (Slot 410 is provided to help facilitate the radial extension of annular flange 415). To place collar member 120 into the locked position with respect to proximal shaft 210, collar member 120 is further displaced distally with respect to proximal shaft 210 until annular flange 415 passes distal locking lip 270 of first locking part 250. After annular flange 415 passes distal locking lip 270, annular flange 415 is forced radially inward to its original position under an inherent biasing force, as shown in FIG. 5e. Once collar member 120 is placed in to the locked position, actuating line 620 may then be removed.

It should be appreciated that collar member 120 is movable distally relative to proximal shaft 210. It is also possible to move proximal shaft 210 proximally with respect to collar member 120 to place collar member 120 into the locked position. For this purpose, a proximal force may be exerted on the ends of actuating line 620 (e.g., by a surgeon), while a suitably dimensioned tool (e.g., insertion tool 900) keeps collar member 120 stationary.

Referring now to FIG. 4, there is seen another exemplary suture anchor 600 according to the present invention. Suture anchor 600 contains features similar to those of suture anchor 100, except that proximal shaft 210 and collar member 120 each include a single suture hole 240, 320, respectively, for receiving both legs 510a, 510b of suture thread 510. The operational sequence for inserting suture anchor 600 into tissue 520 is similar to that for inserting suture anchor 100. (See FIGS. 5a to 5e). When inserting suture anchor 600, however, after being threaded through tissue 950, both legs 510a, 510b of suture thread 510 are inserted through suture holes 240, 320 of inner member 110 and collar member 120. The remaining steps of the operational sequence illustrated in FIGS. 5a to 5e are performed normally.

Figure 7A:
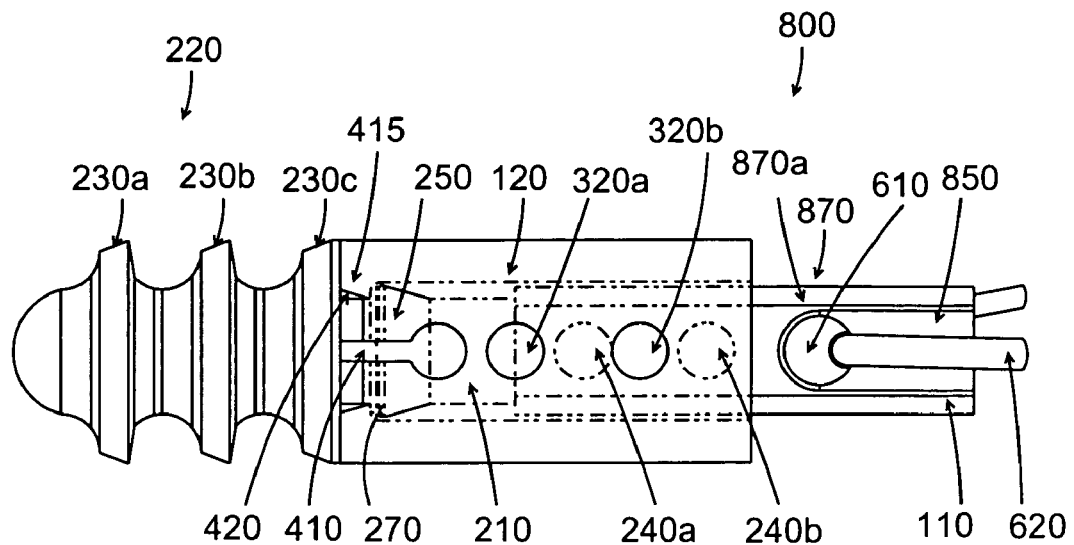
FIGS. 7a and 7b illustrate yet another exemplary knotless suture anchor according to the present invention.
Figure 7B:
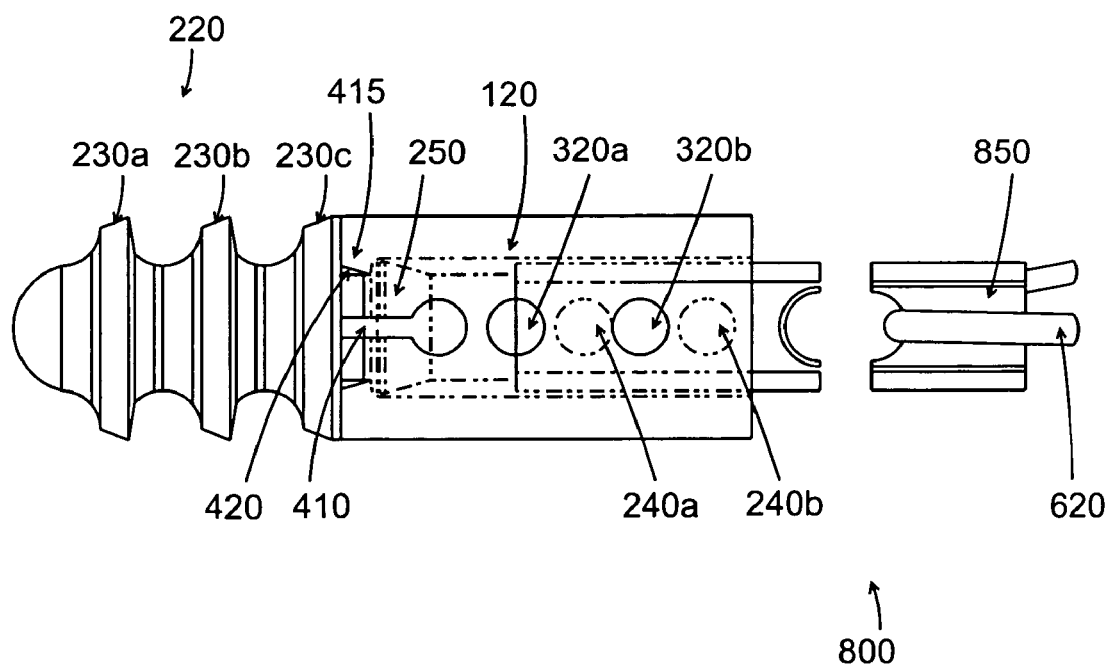

Referring now to FIGS. 7a and 7b, there is seen yet another exemplary suture anchor 800 according to the present invention. Suture anchor 800 contains features similar to those of suture anchor 100, except that proximal shaft 210 of suture anchor 800 includes frangible portion 850. The operational sequence for inserting suture anchor 800 into tissue 520 is similar to that for inserting suture anchor 100. (See FIGS. 5a to 5e). However, in this exemplary embodiment, an excess proximal force is exerted on both ends of actuating line 620, after collar member 120 is placed in to the locked position (see FIG. 5e). The excess force causes frangible portion 850 of proximal shaft 210 to break away, and the frangible portion 850 and actuating line 620 may then be removed (note: the excess proximal force exerted on actuating line 620 is a force greater than that exerted on actuating line 620 when collar member 120 is relatively moved distally into the locked position with respect to proximal shaft 210 of inner member 110). A weakened portion 870, such as perforation 870, may be provided to facilitate disconnection of frangible portion 850 from proximal shaft 210. Although FIGS. 7a and 7b show weakened portion 870 extending through additional hole 610, it should be appreciated that the weakened portion 870 may be provided at other locations on proximal shaft 210 of inner member. For example, weakened portion 870 may be provided distally of additional hole 610 to ensure that frangible portion 850 and suture actuating line 620 remain together while they are removed. Alternatively, weakened portion 870 may be any other type of weakening in proximal shaft 210. For example, weakened portion 870 may include a notch in proximal shaft 210, which forms a portion of reduced diameter, thereby weakening proximal shaft 210 at that point.

FIGS. 8a and 8b shows an additional exemplary knotless suture anchor 1000 in unlocked and locked positions, respectively. Knotless suture anchor 1000 is similar to that of suture anchor 100, except that second locking part 325 of collar member 120 is located at proximal side 310 of collar member 120, and first locking part 250 of shaft 210 is located more proximally on shaft 210 than that of suture anchor 100.

Figure 8C:
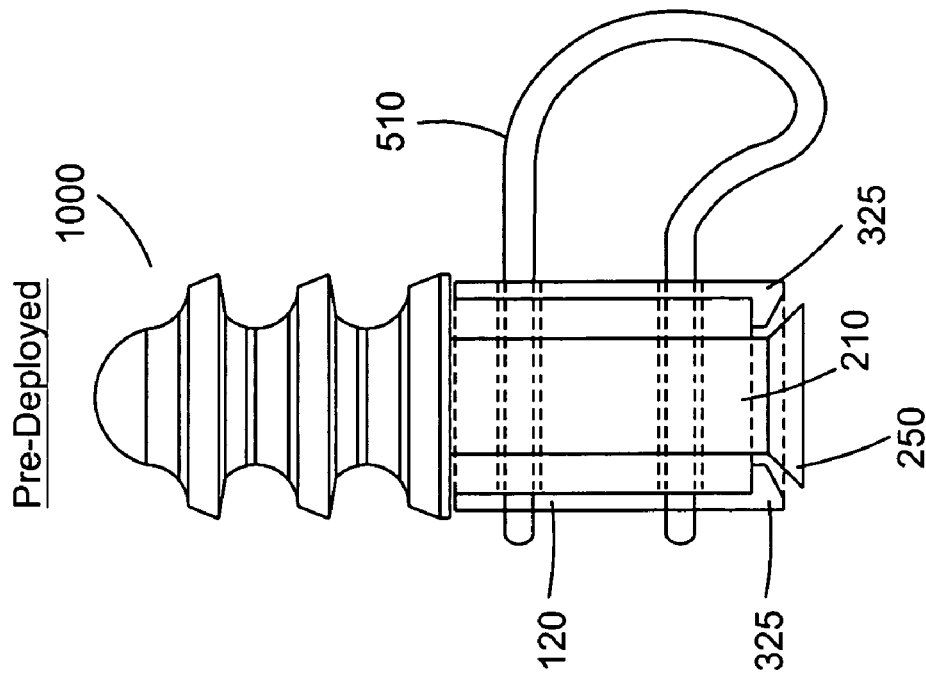
Figure 8D:
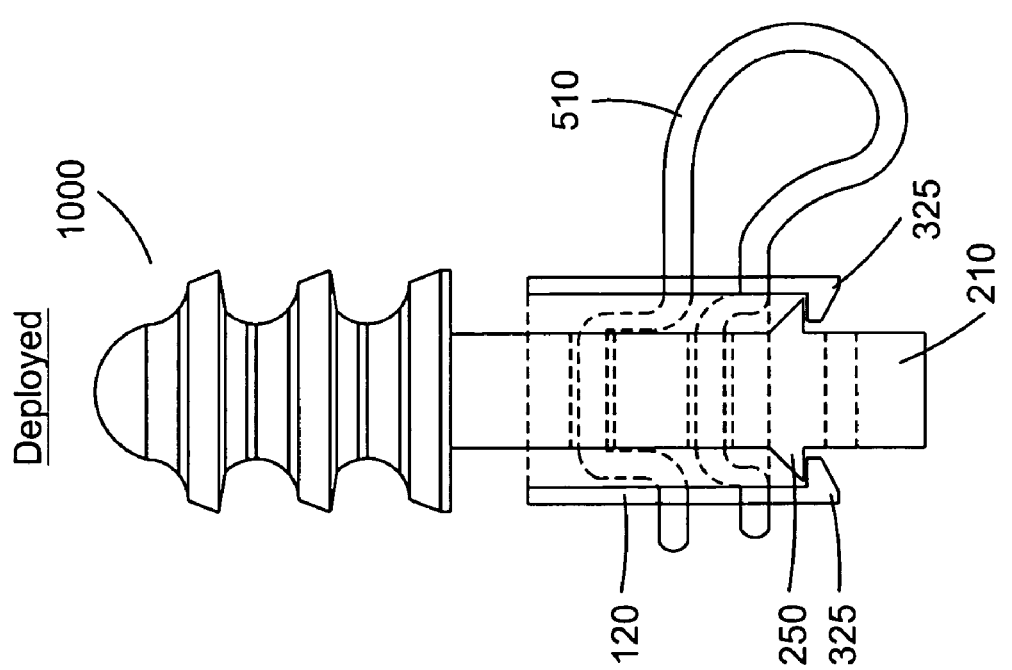

The operational sequence for inserting suture anchor 1000 into tissue 520 is similar to that for inserting suture anchor 100. (See FIGS. 5a to 5e). However, to place collar member 120 into the locked position (see FIG. 8b), collar member 120 is relatively moved proximally (not distally) toward first locking part 250 of proximal shaft 210. Collar member 120 may be relatively moved distally, for example, using a suture anchor insertion tool (not shown) configured to engage with collar member 120 for pulling collar member 120 proximally with respect to proximal shaft 210. While collar member 120 is slid proximally, a distal force may be exerted on proximal shaft 210 to ensure that suture anchor 1000 remains stationary within tissue 520 while collar member 120 is moved proximally into the locked position with respect to proximal shaft 210 of inner member 110. The distal force exerted on the proximal shaft 210 may be effected by a suitably dimensioned tool (not shown) and/or a surgeon. The proximal movement of collar member 120 causes suture holes 320a, 320b of collar member 120 to come out of alignment with suture holes 240a, 240b of inner member 110, thereby causing suture 510 to be frictionally secured between the outer surface of proximal shaft 210 and the inner surface of collar member 120, as shown in FIG. 8b. FIGS. 8c and 8d show a cutaway view of suture anchor 1000 in the unlocked and locked positions, respectively.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A knotless suture anchor for anchoring two free ends of a looped suture thread to tissue without requiring a knot in the suture thread, comprising:
    an inner member including a proximal shaft and a distal securing member, the distal securing member having a structure to secure the distal securing member into a bore hole in tissue and thereby secure the inner member to the tissue, the proximal shaft including first and second holes extending therethrough for receiving the respective two free ends of the suture thread and further having a first locking part; and
    a collar member disposed around the inner member including an axial bore shaped to receive the proximal shaft of the inner member, a second locking part and first and second holes extending through the collar member and respectively assigned to the first and second holes of the proximal shaft of the inner member, the collar member being axially slidable into unlocked and locked positions relative to the proximal shaft of the inner member, the collar member being relatively axially slidable into the locked position only to secure the suture thread;
    wherein the holes of the collar member are aligned with the holes of the proximal shaft of the inner member when the collar member is placed into the unlocked position, the holes of the collar member are misaligned with the holes of the proximal shaft of the inner member when the collar member is placed into the locked position, and the first locking part of the proximal shaft engages with the second locking part of the collar member to axially lock the collar member with respect to the proximal shaft when the collar member is placed into the locked position, the two free ends of the looped suture thread being disposed through the respective holes in the proximal shaft and in the collar member so that the two free ends of the looped suture thread are secured by the misalignment of said holes in the proximal shaft and in the collar member in the locked position.

2. The knotless suture anchor of claim 1, wherein the distal securing member includes at least one annular rib.

3. The knotless suture anchor of claim 1, wherein the first locking part of the proximal shaft includes a flange portion having a sloped proximal surface and a distal locking lip, and the second locking part of the collar member includes a transverse slot, an annular flange extending radially inward, and a countersink portion formed in a distal end of the annular flange.

4. The knotless suture anchor of claim 1, wherein the proximal shaft of the inner member includes an additional hole for receiving an actuating line.

5. The knotless suture anchor of claim 4, wherein the actuating line includes at least one material selected from the group consisting of ultra-high molecular weight polyethylene, Kevlar and Spectra.

6. The knotless suture anchor of claim 4, wherein the actuating line is an additional length of suture thread.

7. The knotless suture anchor of claim 4, wherein the proximal shaft of the inner member includes a frangible portion configured to disconnect at least a portion of the proximal shaft when an excess proximal force is exerted on the actuating line.

8. The knotless suture anchor of claim 1, wherein the suture anchor is bio-absorbable.

9. A method of knotlessly securing two free ends of a looped suture thread to a first tissue, the method comprising:
providing a knotless suture anchor including:
an inner member including a proximal shaft and a distal securing member, the distal securing member having a structure to secure the distal securing member into a bore hole in the first tissue and thereby secure the inner member to the first tissue, the proximal shaft including first and second holes extending therethrough for receiving the respective two free ends of the suture thread and further having a first locking part; and
a collar member disposed around the inner member including an axial bore shaped to receive the proximal shaft of the inner member, a second locking part, and first and second holes extending therethrough and respectively assigned to first and second holes of the proximal shaft of the inner member, the collar member being axially slidable into unlocked and locked positions relative to the proximal shaft of the inner member, the collar member being relatively axially slidable into the locked position only to secure the suture thread;
wherein the holes of the collar member are aligned with the holes of the proximal shaft of the inner member when the collar member is placed into the unlocked position, the holes of the collar member are misaligned with the holes of the proximal shaft of the inner member when the collar member is placed into the locked position, and the first locking part of the proximal shaft engages with the second locking part of the collar member to axially lock the collar member with respect to the proximal shaft when the collar member is placed into the locked position;
placing the collar member of the suture anchor into the unlocked position with respect to the proximal shaft of the inner member;
threading one free end of the suture thread thorough a portion of said second tissue thereby forming the looped suture thread with the second tissue captured in the loop;
threading the two free ends of the suture thread respectively through the first and second holes of the collar member and the aligned first and second holes of the proximal shaft of the inner member;
inserting the knotless suture anchor into the bore hole in the first tissue so that the distal securing member securely engages the first tissue; and
sliding the collar member from the unlocked position to the locked position to frictionally secure the two free ends of the looped suture thread between an outer surface of the proximal shaft and an inner surface of the collar member whereby the second tissue captured in the loop is secured to the first tissue.

10. The method of claim 9, wherein the proximal shaft of the inner member includes an additional hole for receiving an actuating line, the method further comprising:
threading the actuating line through the additional hole of the proximal shaft of the inner member; and
exerting a proximal force on the actuating line to move the collar member relatively with respect to the proximal shaft to place the collar member in the locked position with respect to the proximal shaft of the inner member.

11. The method of claim 10, wherein the actuating line includes at least one material selected from the group consisting of ultra-high molecular weight polyethylene, Kevlar and Spectra.

12. The knotless suture anchor of claim 11, wherein the actuating line is an additional length of suture thread.

13. The method of claim 10, wherein the proximal shaft of the inner member includes a frangible portion configured to disconnect at least a portion of the proximal shaft when an excess proximal force is exerted on the actuating line.

14. The method of claim 9, wherein the knotless suture anchor is bio-absorbable.

* * * * *